United States Patent [19]

Lukacsko et al.

[11] Patent Number: 5,037,815

[45] Date of Patent: Aug. 6, 1991

[54] NON-STEROIDAL ANTI-INFLAMMATORY COMPOSITIONS PROTECTED AGAINST GASTROINTESTINAL INJURY WITH A COMBINATION OF CERTAIN $H_1$- AND $H_2$-RECEPTOR BLOCKERS

[75] Inventors: Alison B. Lukacsko, Robbinsville; Randy J. Koslo, East Windsor; Joseph J. Piala, Metuchen, all of N.J.

[73] Assignee: Bristol-Myers Squibb Co., New York, N.Y.

[21] Appl. No.: 241,803

[22] Filed: Sep. 8, 1988

Related U.S. Application Data

[60] Continuation of Ser. No. 184,525, Jun. 8, 1988, abandoned, which is a division of Ser. No. 867,882, Apr. 29, 1986, Pat. No. 4,757,060, which is a continuation-in-part of Ser. No. 836,264, Mar. 4, 1986, abandoned.

[51] Int. Cl.$^5$ .................... A61K 31/50; A61K 31/55; A61K 31/435; A61K 31/615

[52] U.S. Cl. .................................. 514/162; 514/220; 514/247; 514/277; 514/396; 514/403; 514/420; 514/520; 514/557; 514/570

[58] Field of Search ............... 514/520, 557, 570, 162, 514/396, 420, 220, 277, 403, 247

[56] References Cited

U.S. PATENT DOCUMENTS 4,683,243  7/1987  Sunshine et al. .................... 514/557
4,755,532  7/1988  Sunshine et al. .................... 514/557
4,757,060  7/1988  Lukacsko et al. .................. 514/160

OTHER PUBLICATIONS

Chem. Abst. 101-222131m (1984), 104-45357d (1986) and 104-199614x (1986).

Primary Examiner—Stanley J. Friedman
Attorney, Agent, or Firm—Morton S. Simon

[57] ABSTRACT

A pharmaceutical composition and process for administering non-steroidal drugs which are protected against injury to the gastrointestinal tract by a combination of certain $H_1$- and $H_2$-receptor blockers.

33 Claims, No Drawings

NON-STEROIDAL ANTI-INFLAMMATORY COMPOSITIONS PROTECTED AGAINST GASTROINTESTINAL INJURY WITH A COMBINATION OF CERTAIN $H_1$- AND $H_2$-RECEPTOR BLOCKERS

This is a continuing application of application Ser. No. 184,525 filed June 8, 1988 abandoned which is a divisional application of application Ser. No. 867,882 filed Apr. 29, 1986, U.S. Pat. No. 4,757,060 which was a continuation-in-part of application Ser. No. 836,264 filed Mar. 4, 1986 and now abandoned.

This invention relates to non-steroidal anti-inflammatory drug (hereinafter referred to as NSAID) compositions containing protectants against NSAID-induced gastrointestinal injury and to processes for administering such composition. More particularly, it concerns compositions and processes of the aforesaid type that employ certain combinations of histamine receptor blockers as the protectants. The compositions of this invention are useful in treating conditions and symptoms that are classically treated by the administration of NSAIDs e.g. headache pain, pain and inflammation associated with arthritis and other systemic diseases, elevated body temperatures etc.

Aspirin and other NSAIDs have long been the most popular drugs for the management of pain, inflammation and fever. However, one of the drawbacks in their use is the gastrointestinal injury and/or bleeding that sometimes accompanies their administration to individuals. This becomes a problem where large and sustained doses of NSAIDs must be given to control the symptoms, as for example, in the case of the management of arthritis.

It has now been found that NSAID-induced gastrointestinal injury can be significantly reduced when a combination of histamine receptor blockers and particularly a combination of an $H_1$-receptor blocker selected from the group consisting of ethanolamines, ethylenediamines, alkylamines and piperazines or pharmaceutically acceptable salts thereof and $H_2$-receptor blockers are administered concurrently with the NSAID.

As pointed out in U.S. Patent 4996571 $H_1$- and $H_2$-receptor blockers form two well-known classes of pharmacologically active drugs that serve as blocking agents for histamine at $H_1$- and $H_2$ histamine receptor sites, respectively. Histamine receptor sites have been differentiated on the basis of the classes of antihistamines that can serve to block these sites. The fact that a drug is identified as an antihistamine does not necessarily mean that it will be effective in blocking all the known histamine receptor sites but may in fact be selective so that it will act at one site e.g. $H_1$ site but not at another e.g. $H_2$ site.

It has been reported in prior art that $H_2$ receptor blocking agents or antagonists protect against aspirin-induced lesions in certain laboratory animals. One such study is a report in Gastroenterology Vol. 88, No. 5 part 2. p. 1344. It has also been reported that cyproheptadine has been evaluated as a protectant against aspirin induced gastrointestinal injury (Indian J. Med. Res. 1980, 71, p. 926–32). Although the cyproheptadine may have some $H_1$-receptor antagonist properties, it does not act exclusively at the $H_1$-receptor sites but rather acts predominantly at the serotonin receptor sites.

Aside from the above the present invention has further significant distinctions from the teachings in the Indian Journal. For one thing in this reference the aspirin and the cyproheptadine are not coadministered as would be the case in the present invention. Furthermore the treatment in this reference with cyproheptadine is reported as not modifying the gastric acidity. This is contrary to the observations made in connection with the present invention. Moreover, the cyproheptadine was administered by intraperitoneal injection prior to the intragastric administration of the aspirin. In contrast to this the compositions of the present invention lend themselves to oral administration at which time the NSAID and the combination of said $H_1$- and $H_2$-receptor blockers are coadministered.

As will be pointed out in more detail below it has been found that by employing certain combinations of $H_1$- and $H_2$-histamine receptor blockers as further defined herein that these two act synergistically in their protective effect against NSAID-induced gastrointestinal injury. This was an unexpected result and would not have been anticipated on the basis of the present state of the art.

A number of $H_1$- and $H_2$-receptor blockers are known in the prior art which are useful for the purposes of the present invention. However, not all of the $H_1$-receptors blockers are equally effective in practicing this invention. Those that are useful should also exhibit anticholinergic properties.

By way of illustrating the $H_1$-receptor blockers that may be employed herein mention may be made of the following: ethanolamines (e.g. diphenhydramine or its hydrochloride salt; carbinoxamine or its maleate salt); ethylenediamines (e.g. tripelennamine or its hydrochloride or citrate salts); alkylamines (e.g. chlorpheniramine or its maleate salt, brompheniramine or its maleate salt triprolidine or its hydrochloride); piperazines (e.g. hydroxyzine or its hydrochloride or pamoate salts, cyclizine or its hydrochloride or lactate salts, neclezine or its hydrochloride salts etc. To exemplify the $H_2$-receptor blockers that may be advantageously used in the practice of this invention the following are given: cimetidene, ranitidine, famotidine, etc.

Generally any combination of said $H_1$, and $H_2$-receptor blockers as outlined above are useful for the purpose of this invention. Nevertheless certain combinations of $H_1$- and $H_2$-receptor blockers have been found to be particularly efficacious. Thus the combination of chlorpheniramine plus ranitidine, diphenhydramine plus ranitidine, chlorpheniramine plus cimetidine, and diphenhydramine plus cimetidine are the combinations of choice in the present invention.

The $H_1$- and $H_2$-receptors blockers may be used in the form of their bases or in the form of their pharmaceutically acceptable salts. When employed as salts these will usually be acid addition salts wherein the acid portion may be hydrochloric, maleic, ascorbic, citric, pamoic, lactic, tartaric, etc.

The NSAIDs form a well-known class of drugs that are anti-inflammatory analgesics. These have the common property of inhibiting the formation of prostagladins which have a protective affect on the gastrointestinal mucosa. See Goodman and Gilman "The Pharmacological Basis for Therapeutics" 7th edition, p. 678. It is because of this inhibiting effect that the oral administration of drugs of this class tend to result in gastrointestinal injury and/or bleeding and is at least part of the problem that the present invention seeks to reduce or eliminate.

A number of NSAIDs are known in the prior art to which the present invention has application. The most commonly known group are the salicylates of which aspirin is the prime example. A further group of NSAIDs that have utility in connection with the instant invention are the propionic acid derivatives. Included in this group are ibuprofen, naproxen. A further group of NSAIDs, employable herein are the fenamates and compounds closely related to them structurally. These may be illustrated by such compounds as mefenamic acid, meclofenamate sodium, diclofenac and its sodium salt. Also belonging to the class NSAIDs with which the present invention is concerned are the indole derivatives (e.g. indomethacin); pyrrole alkanoic acid derivatives (e.g. tolmetin); pyrazalone derivatives (e.g. phenylbutazone); oxicams (e.g. piroxicam), etc.

It is contemplated that in the practice of the present invention the NSAID and the histamine receptor blockers will be administered concurrently in a convenient product form. The essential ingredients of such products will be the $H_1$- and $H_2$-receptor blockers and the NSAID. Over and above this these products may also contain other ingredients which will to a large extent depend upon the particular dosage form of the product, e.g. tablets, capsules, powders, suspensions etc.

The quantity of $H_1$-receptor blocker that will be contained in the composition of this invention may vary somewhat. All that is required is that an effective amount be present so that the $H_1$-receptor blocker can make its contribution as a protectant against NSAID induced gastrointestinal injury.

Similarly the quantity of $H_2$ receptor blocker in the present composition may also vary, Again, all that is required is that amount employed be an effective quantity which will enable the $H_2$-receptor blocker to play its part as protectant.

The NSAID will be contained in the composition of this invention at levels at which it is generally found in therapeutic NSAID compositions intended for oral administration. This will usually be a pharmaceutically acceptable analgesic/anti-inflammatory dose.

The quantitative relationship of the NSAID and the $H_1$- and $H_2$-receptor blockers contained in the present products may be expressed on the basis of the daily average dose of the ingredient, e.g. mg/kg of body weight/day. In this case the average daily dose for the ingredients will have the values in the range set forth in the following table:

| Ingredient | General Range | Preferred Range |
| --- | --- | --- |
| NSAID | about 10 mg/kg/day to about 100 mg/kg/day | about 15 mg/kg/day to about 75 mg/kg/day |
| $H_1$-Receptor Blocker | about 2.5 µg/kg/day to about 500 mg/kg/day | about 100 µg/kg/day to about 50 mg/kg/day |
| $H_2$-Receptor Blocker | about 10 µg/kg/day to about 1 g/kg/day | about 0.010 mg/kg/day to about 10 mg/kg/day |

The unit dosage forms for the present products will be formulated for convenient oral administration. Each such unit will generally contain from about 200 mg to about 600 mg of NSAID, from about 0.1 mg to about 70 mg of $H_1$-receptor blocker and from 0.5 mg to about 350 mg of $H_2$-receptor blocker. In formulating these products pharmaceutically acceptable doses of the aforesaid ingredients within the ranges set out above will be employed.

Depending upon the dosage form employed the products of this invention may also contain other adjuvants that may be useful in formulating or administering the particular dosage form. Thus, for example, when administered as a tablet the products of this invention may also contain lubricants, excipients, binding agents, disintegrating agents, flavoring agents, etc. In addition these products may also contain other pharmaceutically active ingredients such as: decongestants, analgesic adjuvants, antihistamines, expectorants, antitussives, diuretics, other analgesics, other anti-inflammatory agents, antipyretics, antirheumatics, anti-oxidants, vasodilators, smooth muscle relaxants, skeletal muscle relaxants, bronchodilators, vitamins, trace minerals, amino acids and biological peptides.

The products of this invention may take a variety of forms. As indicated above they may assume the form of tablets. However, the NSAID and the $H_1$ and $H_2$ receptor blockers may also be in powdered or granular form contained in edible capsules such as gelatin capsules. The present products may also take the form of suspensions or solutions of the above ingredients in a suitable liquid medium or as powders packaged in suitable paper envelopes.

The following Examples are given to further illustrate the present invention. It is to be understood, however, that this invention is no limited thereto.

EXAMPLE 1

| | |
| --- | --- |
| Aspirin | 325 mg |
| Ranitidine hydrochloride | 3.33 mg |
| Chlorpheniramine maleate | 3.33 mg |

The above ingredients are mixed in powdered or granular form and loaded into gelatin capsules.

EXAMPLE 2

| | |
| --- | --- |
| Aspirin | 325 mg |
| Cimetidine hydrochloride | 16.67 mg |
| Chlorpheniramine maleate | 3.33 mg |

Prepared as described in Example 1.

EXAMPLE 3

| | |
| --- | --- |
| Aspirin | 325 mg |
| Cimetidine hydrochloride | 3.33 mg |
| Diphenhyramine hydrochloride | 16.67 mg |

Prepared as described in Example 1.

The following experiments were carried out to test the effectiveness of the combination of $H_1$- and $H_2$-receptor blockers in protecting the stomach against NSAID-induced gastrointestinal injury and to compare any protection afforded by the individual $H_1$- and $H_2$-receptor blockers. In these studies the $H_1$- and $H_2$-receptor blockers are used in the form of the following acid salts: ranitidine HCl, diphenhydramine HCl, chlorpheniramine maleate, cimetidine HCl. A standard dose of 975 mg of aspirin is administered orally to dogs along with, respectively, treatment (a) through (h) as indicated below. The stomach lining of the dogs are examined endoscopically and rated as to the degree of injury. The results are given in the table following the description of the methodology.

| treatment | cimetidine 50 mg | ranitidine 10 mg | diphen- hydramine 50 mg | chlorpheniramine 10 mg |
|---|---|---|---|---|
| a | x | | | |
| b | | x | | |
| c | | | x | |
| d | | | | x |
| e | | x | x | |
| f | x | | x | |
| g | | x | | x |

All test formulations are prepared on the day of the tests. The capsules are placed in the back of the dog's throat. A stomach catheter with attached funnel is positioned in the dog's stomach and 50 ml. of deionized water is administered.

Healthy adult beagle dogs of either sex are selected for testing. Dogs are housed individually in stainless steel cages with grid floors to allow excreta to pass through. Room temperature in the holding rooms and test laboratories is maintained between 65° F. and 85° F. and relative humidity between 30% and 80%. Room lights remain on from 6:00 AM to 4:00 PM.

Each dog is trained to stand in a stanchion with sling support and to accept a bit tied in its mouth. A gastroscope is then passed through the bit into the dog's stomach. This training requires ten days to two weeks in most dogs.

To determine whether a dog is suitable for test purposes, its stomach is examined for a normal mucosa, and its gastric responsiveness to NSAID is evaluated (as under Test Procedure). An acceptable gastric irritation score in the antrum must be 5 or greater, 2 hours after dosage.

Food is withheld from test dogs for 24 hrs. before the test and during the test and water is allowed ad lib. The dogs are moved into a holding area away from the kennel. Fasted dogs of either sex are examined gastroscopically to ensure that their stomachs have normal healthy mucosal linings. The dogs are dosed orally with test formulations, which are flushed into their stomachs with 50 ml. of deionized water. They are then re-examined two and four hours later for gastric petechiae and signs of bleeding according to the following scale:

0 = uniform, pale to dark pink mucosa
1 = darker pink or blotchy mucosa
2 = petechias and/or light red streaks
3 = few small lesions
4 = many or connected small lesions (striations)
5 = few large lesions
6 = many large lesions
7 = massive hemorrhagic damage Severity of injury for each treatment and at each time is calculated as the mean gastric irritation score.

In addition to the endoscopic observation of the gastric mucosa of each dog a qualitative description of gastric fluid is recorded and a pH measurement is made of the gastric fluid. All of these are done 2 hours after administration of the test product.

A base line is established by measuring the various parameters after the administration of 975 mg of aspirin by itself. The resting stomach has an irritation score of 0 and a pH of 5 to 5.5. Aspirin alone produces injury which scores at approximately 5.6 after 2 hours and the gastric pH at this time is about 3.1. After 4 hours these values are 4.0 for the irritation factor and the pH is about 4.7. This indicates that a certain amount of healing takes place between the 2nd and 4th hour after administration.

The results of these tests with respect to the two hour injury data are summarized in the following table below:

TABLE I

| Test Composition | 2 Hr. Score Injury | pH |
|---|---|---|
| aspirin (975 mg) | 5.6 | 3.1 |
| aspirin (975 mg) + ranitidine HCl (10 mg) | 3.5 | 5.3 |
| aspirin (975 mg) + chlorpheniramine maleate (10 mg) | 4.0 | 4.4 |
| aspirin (975 mg) + cimetidine HCl (50 mg) | 2.4 | 5.6 |
| aspirin (975 mg) + diphenhydramine HCl (50 mg) | 4.0 | 3.6 |
| aspirin (975 mg) + ranitidine HCl (10 mg) + diphenhydramine HCl (50 mg) | 0.6 | 5.4 |
| aspirin (975 mg) + ranitidine HCl (10 mg) + chlorpheniramine maleate (10 mg) | 1.6 | 4.7 |
| aspirin (975 mg) + cimetidine HCl (50 mg) + diphenhydramine HCl (50 mg) | 1.0 | 7.0 |

An examination of these data shows that significantly more, synergistic protection is obtained when a combination of an $H_1$-and $H_2$-receptor blocker is employed together with aspirin as compared with the cases in which $H_1$-or $H_2$-receptor blocker, respectively, is issued alone.

A further study was carried out using the same protocol described on pages 9 and 10 above. In this study, a standard dose of 975 mg of aspirin is administered orally to dogs along with the combination of $H_1$- and $H_2$-receptor blockers shown in Table II below. The numbers appearing in the parentheses below each receptor blocker in this table indicates the doses of the respective $H_1$- or $H_2$-receptor blocker employed, expressed in milligrams. The results of this study are summarized in Table II below.

TABLE II

| $H_1$-Receptor Blocker Plus (mg) | $H_2$-Receptor Blocker (mg) | Mean Irritation Score (2 hr) | Equiv. Dose of Ranitidine (mg) | Mean Gastric pH | Mean Gastric pH Equivalent Dose of Ranitidine mg |
|---|---|---|---|---|---|
| Terfenadine (60) | Ranitidine .HCl (10) | 4.75 ± 0.63 | 5.32 | 4.0 ± 1.17 | 14.63 |
| Diphenhydramine .HCl (50) | Ranitidine .HCl (10) | 0.63 ± 0.18 | 40.67 | 5.4 ± 1.14 | 24.67 |
| (25) | (10) | 2.29 ± 0.57 | 26.42 | 5.2 ± 1.13 | 23.24 |
| Triprolidine .HCl (10) | Ranitidine .HCl (10) | 1.67 ± 0.56 | 31.74 | 4.1 ± 1.18 | 15.35 |
| Chlorpheniramine .maleate (10) | Ranitidine .HCl (10) | 1.56 ± 0.38 | 32.69 | 4.7 ± 1.12 | 19.65 |
| Meclezine .2HCl | Ranitidine .HCl | 2.50 ± 0.66 | 24.62 | 4.4 ± 1.18 | 17.50 |

TABLE II-continued

| H$_1$-Receptor Blocker Plus (mg) | H$_2$-Receptor Blocker (mg) | Mean Irritation Score (2 hr) | Equiv. Dose of Ranitidine (mg) | Mean Gastric pH | Mean Gastric pH Equivalent Dose of Ranitidine mg |
|---|---|---|---|---|---|
| (12.5) Tripelennamine .HCl (12.5) | (10) Ranitidine .HCl (10) | 1.33 ± 0.30 | 34.66 | 5.0 ± 1.13 | 21.80 |

As will be noted from Table II when the combination of terfenadine and ranitidine is used along with the aspirin very little if any improvement in irritation reduction is to be noted (compare 4.75±0.63 in Table II and 5.6 value for aspirin alone in Table I). Terfenadine, however, does not fall within the definition of H$_1$-receptor blockers used in the present invention. That is to say, it is not an ethylenediamine, an ethanolamine, an alkylamine or a piperazine H$_1$-receptor blocker. (See American Hospital Formulary Service Drug Information 87 p.2)

In contrast to this, all the other combinations of H$_1$- and H$_2$-receptor blockers in Table II show a decided degree of protection from the gastric irritation commonly induced by the aspirin in the test dose. Furthermore, the "Equivalent Dose of Ranitidine (mg)" data given in Column 4 of Table II are quite revealing and demonstrate that, by and large, the combination of H$_1$- and H$_2$-receptor blockers act syndergistically in this invention in protecting against gastric irritation due to aspirin. The values given in this column are the equivalent amounts of ranitidine (in milligrams) that would be required to give the degree of protection from irritation that is reflected in the values given in column 3 (Mean Irritation Score(2 hr)). Thus, for example, a combination of 10 mg of triprolidine hydrochloride and 10 mg of ranitidine hydrochloride (for a total of 20 mg H$_1$- and H$_2$-receptor blockers) gives the same protection which would require 31.74 mg of ranitidine hydrochloride if the latter were used alone. Similarly, the combination of 10 mg of chlorpheniramine maleate and 10 mg of ranitidine hydrochloride (for a total of 20 mg of H$_1$- and H$_2$-receptor blockers) gives the same protection which would require 32.69 mg of ranitidine hydrochloride if the latter were used alone. Similarly, positive results are demonstrated with other combinations of H$_1$- and H$_2$-receptor blockers encompassed by the present claims.

Similarly, as in clear from Table II the combination of H$_1$- and H$_2$-receptor blockers tested therein act synergistically with respect to the increase in mean gastric pH. This provides extra protection against gastric irritation that would be attributable to increased gastric acidity.

We claim:

1. A NSAID composition having reduced potential for NSAID induced gastrointestinal injury comprising:
   (a) an analgesic or antiinflammatory amount of a NSAID or pharmaceutically acceptable salts thereof;
   (b) a protective amount of
      (i) an H$_1$-receptor blocker selected from the group consisting of ethanolamines, ethylenediamines, alkylamines and piperazines and pharmaceutically acceptable salts thereof; and
      (ii) an H$_2$-receptor blocker or pharmaceutically acceptable salts thereof;

provided that when the NSAID is aspirin, the H$_1$-receptor blocker is other than diphenhydramine or a pharmaceutically acceptable salt thereof.

2. A NSAID composition having reduced potential for NSAID-induced gastrointestinal injury comprising:
   (a) an analgesic or antiinflammatory amount of a NSAID selected from the group consisting of salicylates, propionic acid derivatives, fenamates, indole derivatives, pyrrole alkanoic acid derivatives, pyrazolone derivatives, oxicams and pharmaceutically acceptable salts of each thereof;
   (b) a protective amount of
      (i) an H$_1$-receptor blocker selected from the group consisting of ethanolamines, ethylenediamines, alkylamines, piperazines and pharmaceutically acceptable salts of each thereof; and
      (ii) an H$_2$-receptor blocker selected from the group consisting of cimetidine, ranitidine, famotidine and pharmaceutically acceptable salts of each thereof;

provided that when the NSAID is aspirin, the H$_1$-receptor blocker is other than diphenhydramine or a pharmaceutically acceptable salt thereof.

3. A composition according to claim 2 wherein:
   (a) said NSAID is selected from the group consisting of aspirin, ibuprofen, naproxen, mefenamic acid, meclofenamate sodium, diclofenac and its sodium salt, indomethacin, tolmetin, phenylbutazone, piroxicam and pharmaceutically acceptable salts of each thereof; and
   (b) said H$_1$-receptor blocker is selected from the group consisting of diphenhydramine, carbinoxamine, tripelennamine, chlorpheniramine, brompheniramine, hydroxyzine, cyclizine, triprolidine, neclezine and pharmaceutically acceptable salts of each thereof.

4. A composition according to claim 3 wherein:
   (a) said NSAID is present in the composition in an amount of from about 10 mg to about 100 mg per kg per day, based on the weight of a subject to whom the composition is being administered;
   (b) said H$_1$-receptor blocker is present in the composition in an amount of from about 2.5 μg to about 500 mg per kg per day, based on the weight of a subject to whom the composition is being administered; and
   (c) said H$_2$-receptor blocker is present in the composition in an amount of from about 10 μg to about 1 g per kg per day, based on the weight of a subject to whom the composition is being administered.

5. A composition according to claim 2 wherein said H$_1$-receptor blocker is an alkylamine or a pharmaceutically acceptable salt thereof.

6. A composition according to claim 5 wherein said alkylamine is selected from the group consisting of chlorpheniramine, brompheniramine, triprolidine and pharmaceutically acceptable salts of each thereof.

7. A composition according to claim 6 wherein said alkylamine is chlorpheniramine or a pharmaceutically acceptable salt thereof.

8. A composition according to claim 7 wherein said NSAID is selected from the group consisting of aspirin, ibuprofen and pharmaceutically acceptable salts of each thereof.

9. A composition according to claim 8 wherein said NSAID is aspirin or a pharmaceutically acceptable salt thereof.

10. A composition according to claim 9 wherein said $H_2$-receptor blocker is ranitidine or a pharmaceutically acceptable salt thereof.

11. A composition according to claim 10 wherein:
(a) said aspirin or a pharmaceutically acceptable salt thereof is present in an amount of from about 200 mg to about 600 mg,
(b) said chlorpheniramine or pharmaceutically acceptable salt thereof is present in an amount of from about 0.1 mg to about 70 mg; and
(c) said ranitidine or pharmaceutically acceptable salt thereof is present in an amount of from about 0.5 mg to about 350 mg.

12. A composition according to claim 2 wherein said $H_1$-receptor blocker is an ethanolamine or a pharmaceutically acceptable salt thereof.

13. A composition according to claim 12 wherein said NSAID is selected from the group consisting of aspirin, ibuprofen and a pharmaceutically acceptable salt of each thereof.

14. A composition according to claim 13 wherein:
(a) said NSAID is present in an amount of from about 200 mg to about 600 mg;
(b) said ethanolamine or pharmaceutically acceptable salt thereof is present in an amount from about 0.1 mg to about 70 mg; and
(c) said $H_2$-receptor blocker is present in an amount of from about 0.5 mg to about 350 mg.

15. A composition according to claim 2 wherein said $H_1$-receptor blocker is an ethylenediamine or a pharmaceutically acceptable salt thereof.

16. A composition according to claim 15 wherein said NSAID is selected from the group consisting of aspirin, ibuprofen and a pharmaceutically acceptable salt of each thereof.

17. A composition according to claim 16 wherein:
(a) said NSAID is present in an amount of from about 200 mg to about 600 mg;
(b) said ethylenediamine or pharmaceutically acceptable salt thereof is present in an amount of from about 0.1 mg to about 70 mg; and
(c) said $H_2$-receptor blocker is present in an amount of from about 0.5 mg to about 350 mg.

18. A composition according to claim 2 wherein said $H_1$-receptor blocker is a piperazine or a pharmaceutically acceptable salt thereof.

19. A composition according to claim 18 wherein said NSAID is selected from the group consisting of aspirin, ibuprofen and a pharmaceutically salt of each thereof.

20. A composition according to claim 19 wherein:
(a) Said NSAID is present in an amount of from about 200 mg to about 600 mg;
(b) said piperazine or pharmaceutically acceptable salt thereof is present in an amount of from about 0.1 mg to about 70 mg; and
(c) said $H_2$-receptor blocker is present in an amount of from about 0.5 mg to about 350 mg.

21. A process for reducing the potential of a NSAID or a pharmaceutically acceptable salt thereof to induce gastrointestinal injury which comprises administering to said subject, based on the weight of the subject,
(a) from about 10 mg to about 100 mg per kg per day of a NSAID,
(b) from about 2.5 µg to about 500 mg per kg per day of an $H_1$-receptor blocker; and
(c) from about 10 µg to 1 g per kg per day of an $H_2$-receptor blocker; wherein
(d) said NSAID is selected from the group consisting of salicylates, propionic acid derivatives, fenamates, indole derivatives, pyrrole alkanoic acid derivatives, pyrazolone derivatives, oxicams and pharmaceutically acceptable salts of each thereof;
(e) said $H_1$-receptor blocker is selected from the group consisting of ethanolamines, ethylenediamines, alkylamines, piperazines and pharmaceutically acceptable salts of each thereof, and
(f) said $H_2$-receptor blocker is selected from the group consisting of cimetidine, ranitidine, famotidine and pharmaceutically acceptable salts of each thereof;
provided that when the NSAID is aspirin, said $H_1$-receptor blocker is other than diphenhydramine or a pharmaceutically acceptable salt thereof.

22. A process according to claim 21 wherein:
(a) said NSAID is selected from group consisting of aspirin, ibuprofen, naproxen, mefenamic acid, meclofenamate sodium, diclofenac or its sodium salts, indomethacin, tolmetin, phenylbutazone, piroxicam and pharmaceutically acceptable salts of each thereof; and
(b) said $H_1$-receptor blocker is selected from the group consisting of diphenhydramine, carbinoxamine, tripelennamine, chlorpheniramine, brompheniramine, hydroxyzine, cyclizine, triprolidine, neclezine and pharmaceutically acceptable salts of each thereof.

23. A process according to claim 21 wherein said $H_1$-receptor blocker is an alkylamine or a pharmaceutically acceptable salt thereof.

24. A process according to claim 23 wherein said alkylamine is chlorpheniramine or a pharmaceutically acceptable salt thereof.

25. A process according to claim 24 wherein said NSAID is selected from the group consisting of aspirin, ibuprofen and pharmaceutically acceptable salts of each thereof.

26. A process according to claim 25 wherein said NSAID is aspirin or a pharmaceutically acceptable salt thereof.

27. A process according to claim 26 wherein said $H_2$-receptor blocker is ranitidine or a pharmaceutically acceptable salt thereof.

28. A process according to claim 21 wherein said $H_1$-receptor blocker is an ethanolamine or a pharmaceutically acceptable salt thereof.

29. A process according to claim 28 wherein said NSAID is selected from the group consisting of aspirin, ibuprofen and pharmaceutically acceptable salts of each thereof.

30. A process according to claim 21 wherein said $H_1$-receptor blocker is an ethylenediamine or a pharmaceutically acceptable salt thereof.

31. A process according to claim 30 wherein said NSAID is selected from the group consisting of aspirin, ibuprofen and pharmaceutically acceptable salts of each thereof.

32. A process according to claim 21 wherein said H$_1$-receptor blocker is a piperazine or a pharmaceutically acceptable salt thereof.

33. A process according to claim 32 wherein said NSAID is selected from the group consisting of aspirin, ibuprofen and pharmaceutically acceptable salts of each thereof.

* * * * *